United States Patent [19]
Altiparmakian et al.

[11] 3,978,062
[45] Aug. 31, 1976

[54] ACRIDONE COMPOUNDS

[75] Inventors: Rodolf Altiparmakian, Binningen; Hans Bohler, Rheinfelden, AG, both of Switzerland

[73] Assignee: Sandoz Ltd., Basel, Switzerland

[22] Filed: Jan. 9, 1974

[21] Appl. No.: 432,054

[30] Foreign Application Priority Data
Jan. 16, 1973   Switzerland............................ 562/73
Apr. 16, 1973   Switzerland.......................... 5408/73

[52] U.S. Cl.................................. 260/276; 260/277; 260/279 R; 260/37 R; 260/37 P; 260/37 N; 260/39 P; 260/40 R; 260/40 P; 260/42.21; 106/288 Q

[51] Int. Cl.²...................... C09B 15/00; C09B 1/16

[58] Field of Search............................ 260/276, 277

[56] References Cited
FOREIGN PATENTS OR APPLICATIONS
596,801   8/1959   Italy
837,481   2/1939   France................................. 260/276
188,225   3/1937   Switzerland
188,226   3/1937   Switzerland

OTHER PUBLICATIONS

Kirk–Othmer, Encyclopedia of Chemical Technology, 2nd Ed., Organic Pigments pp. 555–556, 568–569 (1968).

Lehmstadt et al., Chem. Berichte 70B 1526–1538 (1937), pp. 1526–1533 relied on.

*Primary Examiner*—Nicholas S. Rizzo
*Assistant Examiner*—Diana G. Rivers
*Attorney, Agent, or Firm*—Gerald D. Sharkin; Richard E. Vila; Joseph J. Borovian

[57] ABSTRACT

Disclosed are anthraquinonylamino-nitroacridones, their production and their use as pigments, particularly their use in pigmenting paper, plastics and as pigments in surface coating media.

7 Claims, No Drawings

ACRIDONE COMPOUNDS

The invention relates to acridone compounds. The invention relates to compounds of formula I,

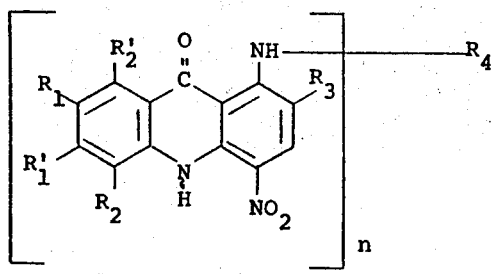

I in which either $R_1$ and $R_1'$, independently, signify a hydrogen or halogen atom or a nitro, cyano, methyl, alkoxy, aminocarbonyl, alkylcarbonylamino, benzoylamino, phenylamino-carbonyl, alkylamino or phenylamino radical, or $R_1$ and $R_1'$, together, signify a radical of formula a,

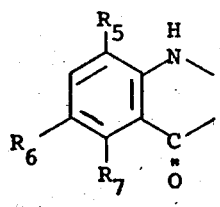

a in which $R_5$ signifies a hydrogen atom or a nitro group,
$R_6$ signifies a hydrogen or halogen atom, and
$R_7$ signifies hydrogen, an unsubstituted amino radical or an amino radical substituted by alkyl, phenyl, benzoyl or anthraquinonyl, or $R_1$ and $R_1'$, together, signify a radical of formula b,

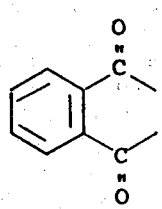

b $R_2$, $R_2'$ and $R_3$, independently, signify a hydrogen or halogen atom,
$n$ signifies 1 or 2, $R_4$ signifies an anthraquinonyl (when $n$ signifies 1) or an anthraquinonylene (when $n$ signifies 2) radical, each of which is unsubstituted or substituted by up to 2 substituents selected from halogen, nitro, alkoxy, amino, alkylamino, phenylamino or benzoylamino, any phenyl radical in the compounds of formula I being unsubstituted, substituted by up to 3 halogen atoms or by a methyl, nitro or alkoxy group, any alkyl or alkoxy radical in the compounds of formula I being of 1 to 4 carbon atoms.

By the term "halogen", as used herein, is to be understood fluorine, chlorine and bromine, chlorine and bromine being preferred.

Where $R_1$ and $R_1'$, together, signify a radical of formula b, as defined above, in such radical the carbonyl groups are preferably in a trans-position relative to one another.

The anthraquinonyl(ene) radical(s) are preferably bound to the acridone molecule through an α-position of such radical(s).

Any substituent on the anthraquinonyl(ene) radical(s) are, with the exception of halogen substituents, preferably bound at α-positions of such radical(s).

Preferred compounds of formula I are the compounds of formula I',

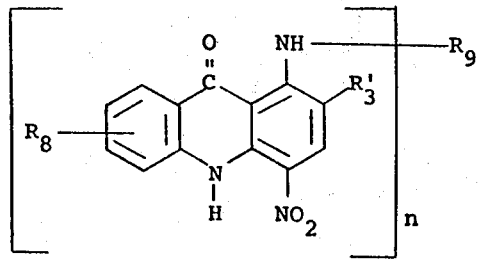

I' in which $R_3'$ signifies a hydrogen, chlorine or bromine atom,
$R_8$ signifies hydrogen, chlorine or bromine atom or a methyl, methoxy, acetylamino or nitro radical and is bound in one of the β-positions, $n$ signifies 1 or 2, and
$R_9$ signifies an anthraquinonyl (where $n$ signifies 1) or an anthraquinonylene (where $n$ signifies 2) radical, which radical is unsubstituted or substituted by up to two substituents selected from chlorine and bromine atoms and methoxy, ethoxy, methylamino, phenylamino and benzoylamino radicals.

Further preferred compounds of formula I are the compounds of formula I'',

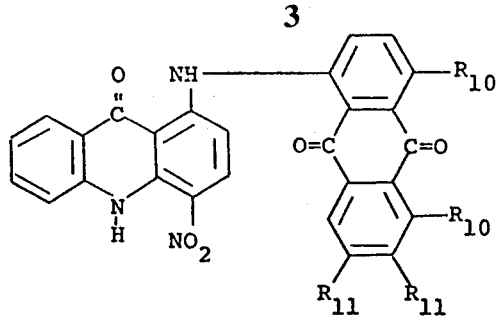

I'' in which the $R_{10}$'s both signify hydrogen or one signifies hydrogen, the other signifies a benzoylamino, phenylamino or methoxy radical, and the $R_{11}$'s, independently, signify hydrogen, chlorine or bromine.

The invention also provides a process for the production of compounds of formula I, characterised by condensing a compound of formula II,

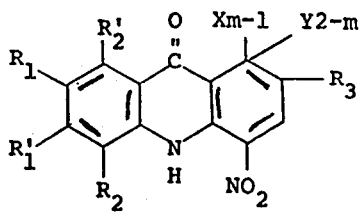

II in which $R_1$, $R_1'$, $R_2$, $R_2'$ and $R_3$ are as defined above, with a compound of formula III,

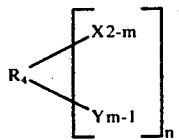

III where $R_4$ and $n$ are as defined above,

X signifying chlorine or bromine,

Y signifying $-NH_2$, and $m$ signifying 1 or 2.

In such process, the mole ratio of the compound of formula II to the compound of formula III is preferably $n:1$.

In the compounds of formulae II and III, $m$ preferably signifies 2.

The process is conveniently carried out in an inert organic solvent, such as in a mixture of xylenes or in nitrobenzene. A suitable reaction temperature is from 160° to 210°C. The process is preferably carried out in the presence of a basic condensation catalyst or an acid binding agent, e.g. sodium or potassium carbonate or bicarbonate. Where, in the compounds of formulae II and III, m signifies 1, the process is advantageously carried out in the presence of a copper catalyst, e.g. in the form of a cuprous salt or powdered copper.

The resulting compounds of formula I may be isolated and purified using conventional techniques.

The compounds of formulae II and III are either known or may be obtained in conventional manner from available starting materials.

The compound of formula Iz,

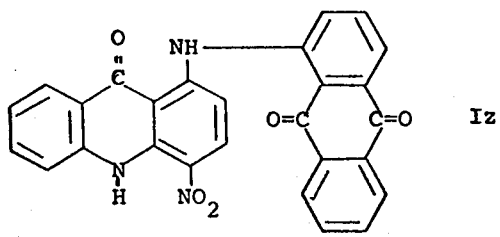

Iz is disclosed by K. Lehmstedt et al. in Berichte der deutchen chemischen Gesellschaft 70B (1937), pages 1526 to 1538, but to our best belief is not known as, nor has it been proposed as, a pigment.

The compounds of formula I are indicated for use as pigments.

The invention provides a process for pigmenting plastics or synthetic resin material in the mass, which process comprises incorporating in such mass an effective amount of a compound of formula I, as defined above.

The incorporation of the compound of formula I may be carried out in conventional manner, e.g. with or without the use of solvents. The amount of compound of formula I incorporated may vary within wide limits, as is conventional in the art, and will depend on the particular compound and the desired depth of shade. The compound of formula I may be pre-conditioned in conventional manner before incorporation in the material. In a preferred method, the compound is subjected to salt or sand grinding in the presence of a small quantity of the material to be pigmented and in an organic solvent for such material. The compound is ground until obtaining an average particle size of less than $1\mu$, after which the grinding agents are separated, e.g. by filtration, from the ground mass. The dispersion so produced is then incorporated into the mass of molten material to be pigmented, or stirred into a solution thereof. The resulting material may then be processed by conventional methods, e.g. by extrusion into sheet or other forms or by spinning into fibers, which fibers may then be further processed into yarns and other textile substrates.

As examples of preferred plastic materials may be given polyethylene, propathene, polystyrene, polyvinylchloride, rubber, artificial leather, viscose, polyacrylonitrile, aromatic polyesters and cellulose acetate.

The compounds of formula I are also indicated for use in other pigment applications, particularly in the production of surface coatings such as paints, either of water or oil base, varnishes and laquers, as well as in the preparation of pigment printing pastes and in the pigmenting of paper in the stock. For such uses, the compounds of formula I are again employed in conventional manner and in conventional amounts.

The compounds of formula I, when used as above, show notable light and heat fastness properties as well as fastness to varnishings, migration and solvents. They have particularly notable distributability properties in plastics in the mass.

The following Examples, in which all parts and percentages are by weight and the temperatures in degrees Centigrade, illustrate the invention.

EXAMPLE 1

5.5 Parts 1-chloro-4-nitroacridone, 4.5 parts 1-amino-anthraquinone and 3.6 parts potassium carbonate in 40 parts nitrobenzene are heated to 200° in 20 minutes with stirring. On cooling, the orange-coloured, crystalline reaction product is filtered, washed with ethyl alcohol, suspended in water, boiled for 30 minutes, filtered while hot, washed with hot water and dried to give the compound of formula

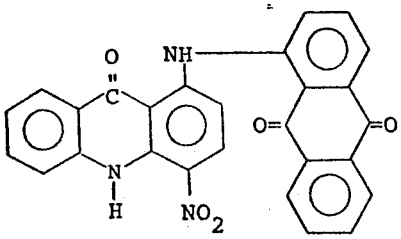

After grinding with, for example, sodium chloride or sodium sulphate and acetone, the compound may be used as a pigment in any conventional way. For additional purification it may also be treated with, for example, dimethyl formamide or trichlorobenzene at temperature around 150°.

APPLICATION EXAMPLE A

Dyeing of Polyvinyl Chloride in the Mass 1.5 Parts 1-($\alpha$-anthraquinoylamino)-4-nitroacridone, the product of Example 1, are first intimately mixed with 3 parts PVC mass by grinding them together and are subsequently well mixed with 48.5 more parts of the same PVC mass. The PVC mass is of the following composition:
- 65 parts polyvinyl chloride emulsion
- 32 parts dioctyl phthalate
- 3 parts standard epoxy plasticizer
- 1.5 parts standard stabilizer (barium-cadmium complex), and
- 0.5 parts standard chelate former.

The mixture is treated on a roller frame with friction rollers at 160° for improved pigment distribution for 8 minutes (one roller rotates at 20, the other at 25 revolutions per minute) and the sheet of 0.3 mm obtained is doffed. The sheet shows an orange dyeing.

A transparent orange-coloured film is obtained when 5 parts of the above sheet are processes according to the described way with another 45 parts of the PVC mass mentioned above.

A pastel-coloured orange sheet is obtained when 5 parts of sheet according to the above, 5.4 parts titanium dioxide pigment and 45 parts PVC mass as described above, are treated in the above-described way.

APPLICATION EXAMPLE B

Varnish Preparation

2 Parts of the pigment of Example 1, the pigment having been salt-ground by the conventional method, are ground with 48 parts of a varnish of the following composition in a ball mill.
- 43.88 parts of a 60% solution of a alkyde-melamine formaldehyde resin in xylene,
- 17.18 parts of a 65% melamine resin solution in butanol,
- 4.57 parts butanol,
- 31.37 parts xylene, and
- 7 parts ethyl glycol acetate.

After the pigmented varnish is separated from the balls by means of a nylon filter, an aluminium sheet (on card-board) is spray-varnished with this full-shade preparation. The sheet thus varnished is allowed to dry in the air for 15 minutes. Subsequently it is stoved at 140° for 30 minutes. The film obtained is of bright orange colour with notable fastness to light and migration.

APPLICATION EXAMPLE C

Pigmentation of Polyacrylonitrile in the Mass
Preparation of the Pigment Dispersion 2 Parts of the dry pigment obtained according to Example 1 are ground with 2 parts powdered polyacrylonitrile, 35 parts dimethyl formamide and 35 parts quartzite grinding pebbles (1 mm diameter) at room temperature until the average diameter of the pigment particles is less than 1$\mu$. The dispersion obtained is separated from the quartzite pebbles by filtration, which are then washed with 150 parts dimethyl formamide.

Preparation of the Spinning Mass

198 Parts powdered polyacrylonitrile are dissolved in 550 parts dimethyl formamide in a conventional spinning apparatus at 50° under a nitrogen atmosphere with stirring. After 30 minutes, the dispersion produced above is entered with stirring and the container rinsed with 65 parts dimethyl formamide.

Production of the Dyed Fibers

The spinning mass produced above is extruded through a spinning nozzle into a spinning bath consisting of a 50:50 parts water/dimethyl formamide mixture. A first doffing cylinder conveys the fibers at a speed of 4 meters/minute to a second spinning bath (water temperature 95°), a second doffing cylinder conveys the fibers at 18 meters/minute to a third spinning bath of water in which 5% of a cation-active condensation product of a fatty acid are dissolved, and a third doffing cylinder lifts the fibers at 27 meters/minute from this last bath. Subsequently, the fibers are conveyed over a drying roll at 180° and a rate of feed of 24 meters/minute.

The fibers thus produced are processed into textile surfaces by conventional methods. The fiber material shows an orange dyeing with the fastness properties mentioned above.

EXAMPLE 2

A mixture of 5.5 parts 1-chloro-4-nitroacridone, 6.9 parts 1-amino-5-benzoylaminoanthraquinone, 3.6 parts potassium carbonate and 50 parts nitrobenzene are raised to 180°–190° in 30 minutes with stirring. On cooling the condensation product is filtered at room temperature, washed with ethanol and dried. In order to free it from inorganic salts, it is then boiled in 100 parts water, filtered again and dried. The pigment thus obtained in pure form is of formula

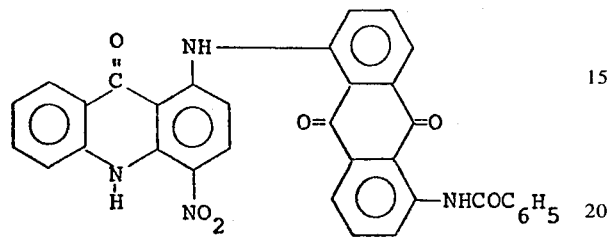

and may be further purified by boiling in dimethyl formamide for 1 hour, filtration at 100°, washing first with dimethyl formamide and subsequently with ethanol and drying.

Polyvinyl chloride dyed with this pigment according to Application Example A, above, has a bluish red shade of notable light fastness properties.

The pigments of formula I listed in the Table below are produced according to Example 1 or 2.

Table

| Ex. No. | $R_1$ | $R_1'$ | $R_2$ | $R_3$ | $R_4$ | n | Shade in Polyvinyl-chloride |
|---|---|---|---|---|---|---|---|
| 3 | H | H | H | H | 4-Benzoylaminoanthraquinonyl-1 | 1 | Bluish red |
| 4 | H | H | H | H | 4-Methoxyanthraquinonyl-1 | 1 | Bluish red |
| 5 | H | H | H | H | 4-Phenylaminoanthraquinonyl-1 | 1 | grey |
| 6 | H | H | H | H | 6,7-Dichloranthraquinonyl-1 | 1 | red |
| 7 | H | H | H | H | 1,4-Anthraquinonylene | 2 | Bluish red |
| 8 | H | H | H | H | 1-Chloranthraquinonyl-2 | 1 | orange |
| 9 | Br | H | H | H | Anthraquinonyl-1 | 1 | orange |
| 10 | H | Cl | H | H | " | 1 | orange |
| 11 | H | H | H | H | Anthraquinonyl-2 | 1 | Brown |
| 12 | H | H | H | H | 4-Methylaminoanthraquinonyl-1 | 1 | grey |
| 13 | $-NO_2$ | H | H | H | Anthraquinonyl-1 | 1 | yellowish red |
| 14 | H | H | H | Br | " | 1 | orange |
| 15 | $-CH_3$ | H | H | H | " | 1 | orange |
| 16 | " | H | H | Cl | " | 1 | red |
| 17 | $-NHCOCH_3$ | H | H | H | " | 1 | yellowish red |
| 18 | Cl | Cl | Cl | H | " | 1 | orange |
| 19 | $-OCH_3$ | H | H | H | " | 1 | red |

The following pigments are also produced in analogy with the method described in Example 1.

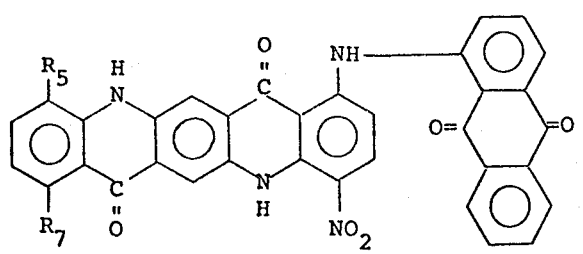

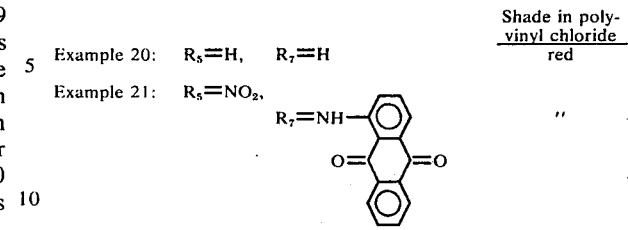

| | | | Shade in polyvinyl chloride |
|---|---|---|---|
| Example 20: | $R_5=H$, | $R_7=H$ | red |
| Example 21: | $R_5=NO_2$, | $R_7=NH-$... | " |

What is claimed is:
1. A compound of formula Ia',

$$Ia'$$

in which $R_3'$ signifies a hydrogen, chlorine or bromine atom, $R_8$ signifies a hydrogen, chlorine or bromine atom or a methyl, methoxy, acetylamino or nitro radical and is bound in one of the β-positions, n signifies 1 or 2, and $R_9$ signifies an anthraquinonyl (where n signifies 1) or an anthraquinonylene (where n signifies 2) radical, which radical is unsubstituted or substituted by up to two substituents selected from chlorine and bromine atoms and methoxy, ethoxy, methylamino, phenylamino and benzoylamino radicals, with the proviso that when $R_3'$ and $R_8$ both signify hydrogen and n signifies 1, $R_9$ signifies other than an unsubstituted 1-anthraquinonyl radical.

2. A compound of claim 1, wherein $n$ signifies 1.
3. A compound of claim 1, wherein $n$ signifies 2.
4. A compound of formula Ia'',

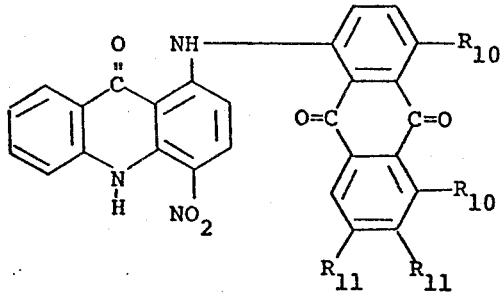

in which the $R_{10}$'s both signify hydrogen or one signifies hydrogen, the other signifies a benzoylamino, phenylamino or methoxy radical, and the $R_{11}$'s, independently, signify hydrogen, chlorine or bromine.

with the proviso that the $R_{10}$'s and $R_{11}$'s do not each signify hydrogen.

5. A compound of claim 4 and of formula

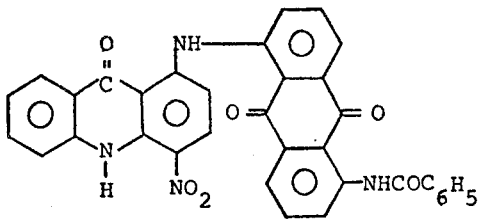

6. A compound of claim 4 and of formula

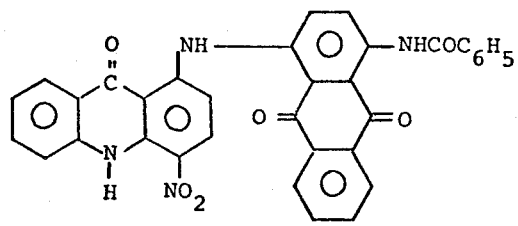

7. A compound of claim 4 and of formula

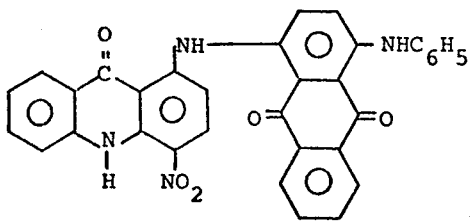

* * * * *